United States Patent [19]

Drewlow

[11] Patent Number: Plant 6,632

[45] Date of Patent: Feb. 28, 1989

[54] KALANCHOE PLANT NAMED GOLDSTRIKE

[75] Inventor: Lyndon W. Drewlow, Ashtabula, Ohio

[73] Assignee: Mikkelsens, Inc., Ashtabula, Ohio

[21] Appl. No.: 104,370

[22] Filed: Oct. 5, 1987

[51] Int. Cl.[4] ..... A01H 5/00

[52] U.S. Cl. ..... Plt./68

[58] Field of Search ..... Plt./68

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A new and distinct cultivar of Kalanchoe named Goldstrike, having golden yellow flowers, vigorous and compact growth habit, floriferous habit, excellent upright basal branching, no delay under high temperatures, and its excellent keeping qualities.

1 Drawing Sheet

The present invention relates to a new and distinctive cultivar of Kalanchoe plant, botanically known as *Kalanchoe blossfeldiana,* and known by the cultivar name Goldstrike. Goldstrike was developed by me through controlled breeding in Ashtabula, Ohio by crossing Mikkelsen Seedling 82-661-1, the seed parent, with Mikkelsen Seedling 82-576-3, the pollen parent.

Asexual reproduction by me at Ashtabula, Ohio of stem cuttings of Goldstrike, of a selection from the progeny of the stated cross, has shown that the unique features of this new Kalanchoe are stabilized and are reproduced true to type in successive propagations.

The following characteristics distinguish Goldstrike from both its parent varieties and other cultivated Kalanchoes of this type known and used in the floriculture industry:

1. Goldstrike is characterized by its golden yellow flowers, as compared to the yellow flower color of Fortyniner (U.S. Plant Pat. No. 5,256), Helios (disclosed in a pending application), and Firefly (U.S. Plant Pat. No. 4,728).

2. Goldstrike is similar in flowering maturity to Helios and one week earlier than Firefly and Fortyniner.

3. Goldstrike is similar in height to Fortyniner, but more compact than either Firefly or Helios.

4. Basal branching is superior to Firefly and similar to Fortyniner and Helios.

5. Flower size of Goldstrike is similar to Helios and slightly smaller in size (but more numerous in number) than Fortyniner and Firefly.

6. Flower clusters of Goldstrike are dense and large, with a large number of branches in the head, similar to Helios. Both Fortyniner and Firefly have more open clusters with less branching.

7. Leaf size of Goldstrike is smaller than Firefly, similar to Helios, but larger than Fortyniner.

8. Helios has a yellow green leaf which is similar in color to Firefly and Helios, with Fortyniner having a darker green leaf.

9. The leaf margins are crenate with a shallow cut similar to Firefly and Fortyniner. The margin of Helios is more deeply cut.

10. Goldstrike has excellent keeping quality under high light and temperatures, comparable to Helios. Fortyniner and Firefly have inferior keeping quality.

The accompanying colored photograph illustrates in top perspective view the overall appearance of Goldstrike, with colors being as true as it is reasonably possible to obtain in a colored reproduction of this type.

The following is a detailed description of Goldstrike based on plants produced under commercial practices in Ashtabula, Ohio under greenhouse conditions during the summer. Color references are made to The Royal Horticultural Society Colour Chart, except where general colors of ordinary dictionary significance are used.

Parentage: Controlled cross between female Mikkelsen Seedling 82-661-1 and male parent Mikkelsen Seedling 82-576-3.

Propagation:

(A) *Type cutting.*—2 cm long stem cutting.

(B) *Time to root.*—10 days at 21° C. summer. 14 days at 21° C. winter.

(C) *Rooting habit.*—Abundant; fine, fibrous roots.

Plant description:

(A) *Form.*—Semi-compact, upright growth with good basal branching, with almost every node developing a branch. Growing and scheduling practices can produce a small plant in a 10 cm pot or a larger plant in a 12 cm pot.

(B) *Habit of growth.*—Vigorous grower, basal branches produce a full flower head but are very upright whereby the bottom half of plants has few flowers.

(C) *Foliage.*—Leaves simple, opposite. (1) Size: Average full grown leaf of a flowering plant in a 10 cm pot is 105 mm long and 70 mm wide. (2) Shape: Oblong to ovate, apex obtuse, base acute. (3) Texture: Glabrous, succulent, coriaceous. (4) Margin: Crenate. (5) Color: Young foliage, top side 146A, under side 147C. Mature foliage, top side 147A, under side 147B.

Flowering description:

(A) *Flowering habits.*—Inflorescence is a cyme with the terminal flower of the main axis opening first, followed continuously by terminal flowers of the developing side branches.

(B) *Natural flowering season.*—Early January. Flowering time under controlled daylength at 20° C. in summer is 10 weeks; in winter is 12 weeks. Flowering time depends on temperature, light intensity and other growing conditions.

(C) *Flower buds.*—Elliptical to oblong, up to 10 mm long, developing to tubular as flower petals mature, sheathed with four green sepals; corolla at maturity is 6 mm long.

(D) *Flowers borne.*—On compound dichasial cymes with primary peduncle 4 mm in diameter. Peduncle length depends on growing conditions and B-9 application. Pedicles are up to 10 mm long.

(E) *Quantity of flowers.*—Very floriferous with main axis having over 100 flowers and 6–8 side branches having 25 or more flowers.

(F) *Petals.*—(1) Shape: Almost round, top cuspidate. (2) Color: Top side, when opening, 15A, fading to 16B; under side 16C. (3) Number of petals: 4.

(G) *Reproductive organs.*—(1) Stamens: Eight (8) in number. (a) Anther shape: Flat, elliptical, color deep yellow. (b) Filament color: Light green. (c)

Pollen color: Deep yellow. (2) Pistils. (a) Stigma shape: Flat, color whitish green. (b) Style color: Light green. (c) Ovaries: 4 in number, size 5 mm, color green.

Disease resistance: No disease problems observed to date.

Other important characteristics: Goldstrike does not heat delay when high temperatures build up under blackcloth during short day treatment to induce flowering.

I claim:

1. A new and distinct cultivar of Kalanchoe plant named Goldstrike, as described and illustrated.

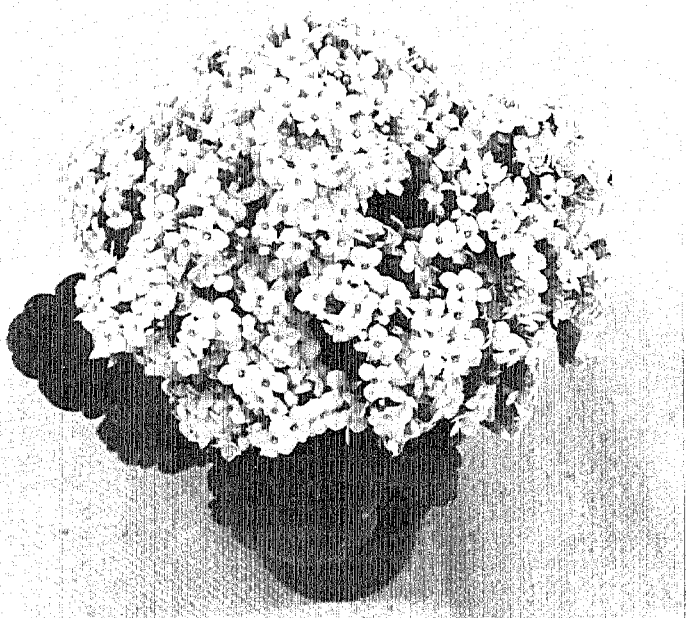

* * * * *